United States Patent
Baca et al.

(10) Patent No.: US 7,160,370 B2
(45) Date of Patent: Jan. 9, 2007

(54) SYSTEMS AND METHODS FOR CONTAMINANT DETECTION WITHIN A FLUID, ULTRAVIOLET TREATMENT AND STATUS NOTIFICATION

(75) Inventors: A. Michael Baca, Albuquerque, NM (US); Luis M. Ortiz, Albuquerque, NM (US); Thomas A. Crow, Albuquerque, NM (US); Donald W. Wichers, Albuquerque, NM (US)

(73) Assignee: SaiTech Corporation NM (US)

( * ) Notice: Subject to any disclaimer, the term of this patent is extended or adjusted under 35 U.S.C. 154(b) by 74 days.

(21) Appl. No.: 10/810,973

(22) Filed: Mar. 25, 2004

(65) Prior Publication Data

US 2006/0207431 A1    Sep. 21, 2006

Related U.S. Application Data

(63) Continuation-in-part of application No. 10/029,444, filed on Dec. 21, 2001, now Pat. No. 6,740,244, and a continuation-in-part of application No. 10/389,355, filed on Mar. 13, 2003.

(60) Provisional application No. 60/364,509, filed on Mar. 14, 2002, provisional application No. 60/257,430, filed on Dec. 22, 2000.

(51) Int. Cl.
*C02F 1/30* (2006.01)
*C02F 1/32* (2006.01)

(52) U.S. Cl. ............................ 96/224; 210/748; 210/97

(58) Field of Classification Search ................ 210/739, 210/748, 764, 87, 97, 198.1, 205; 96/224; 422/24, 186.3; 250/432 R, 435, 436, 437
See application file for complete search history.

(56) References Cited

U.S. PATENT DOCUMENTS

| | | | |
|---|---|---|---|
| 4,661,264 A * | 4/1987 | Goudy, Jr. ................... | 210/748 |
| 5,376,281 A * | 12/1994 | Safta .......................... | 210/748 |
| 5,480,562 A * | 1/1996 | Lemelson .................... | 210/745 |
| 5,874,741 A * | 2/1999 | Matschke .................... | 250/435 |
| 6,468,433 B1 * | 10/2002 | Tribelski ..................... | 210/748 |
| 6,508,989 B1 * | 1/2003 | Urrusti et al. .............. | 422/121 |
| 6,740,244 B1 * | 5/2004 | Baca ........................... | 210/748 |
| 6,767,458 B1 * | 7/2004 | Safta .......................... | 210/202 |

* cited by examiner

*Primary Examiner*—Frank M. Lawrence (57) ABSTRACT

A fluid-borne (e.g., water, air) biological and chemical hazard detection and treatment system can include sensors (e.g., flow rate, contaminant detectors), treatment using ultraviolet laser-emitted light, can be microprocessor controlled and can communicate and be controlled over data networks. Treatment and detection systems can be deployed at various stages along a fluid distribution system, allowing for protection coverage and redundancy. During treatment, fluid enters into and/or passes through a "treatment area" wherein the fluid is subjected to light emanating from a laser at wavelengths within the ultraviolet range. DNA for microorganisms contained within fluid (including blood) are reactive to laser light as they pass through treatment areas and are rendered un-infective. Treatment systems can be staged in close proximity, providing more than one treatment area and associated light sources to a fluid stream. Such staging can provide for concentrated redundancy prior to its delivery to the intended point of use.

7 Claims, 6 Drawing Sheets

SYSTEMS AND METHODS FOR CONTAMINANT DETECTION WITHIN A FLUID, ULTRAVIOLET TREATMENT AND STATUS NOTIFICATION

APPLICATION PRIORITY

This patent document is a Continuation-in-Part of Non-provisional patent application, Ser. No. 10/029,444, filed Dec. 21, 2001, now U.S. Pat. No. 6,740,244, entitled "NEAR POINT OF USE LASER WATER TREATMENT," which further claims priority to a Provisional Patent Application, Ser. No. 60/257,430, filed Dec. 22, 2000, entitled "NEAR POINT OF USE LASER WATER TREATMENT." This patent document is also a Continuation-in-Part of Non-provisional patent application, Ser. No. 10/389,355, filed Mar. 13, 2003, entitled "LASER WATER DETECTION, TREATMENT AND NOTIFICATION SYSTEMS AND METHODS," which further claims priority to a Provisional Patent Application, Ser. No. 60/364,509, filed Mar. 14, 2002, entitled "LASER WATER DETECTION, TREATMENT AND NOTIFICATION SYSTEMS AND METHODS."

FIELD OF THE INVENTION

The present invention is generally related to liquid treatment systems and methods and, more particularly, to the treatment of fluid such as air, blood and water, using ultraviolet laser technology.

BACKGROUND

The water supplied to U.S. communities is potentially vulnerable to terrorist attacks by insertion of biological agents. The possibility of such attacks is now of considerable concern. Biological agents could be a threat if they were inserted at critical points in a water supply system; theoretically, they could cause a large number of casualties.

History repeats itself. Deliberate chemical or biological contamination of air and water supplies has been a common occurrence throughout history. Attacks have ranged from the crude dumping of human and animal cadavers into water supplies to well orchestrated contamination with anthrax and cholera. Cyanide has been used as a deadly waterborne and airborne poison for thousands of years. In ancient Rome, Nero eliminated his enemies with cherry laurel water (cyanide is the chief toxic ingredient). In the U.S. Civil War, Confederate soldiers shot and left farm animals to rot in ponds during General Sherman's march, compromising the Union water supply. During World War II, the Japanese attacked at least 11 Chinese cities, intending to contaminate food and water supplies with anthrax, cholera, and various other bacteria. Hitler's forces also released sewage into a Bohemia reservoir, deliberately sickening the rival population.

Terrorists are more than ever likely to use chemical or biological weapons (CW/BW). The Aum Shinrikyo Cult attacked a Tokyo subway with sarin gas in 1995 and they are known to have produced and unsuccessfully attempted to use anthrax and botulism toxin nine times as well. In 1985 the Rajneesh religious cult sickened 750 people in The Dalles, Oreg., by spreading salmonella bacteria on local salad bars. In an unprecedented violation of the Geneva Conventions, Yugoslav federal forces, or those allied with them, appear to have poisoned wells throughout Kosovo in October/November 1998. Those responsible dumped animal carcasses and hazardous materials (chemicals like paints, oil, and gasoline) into seventy percent of area wells, deliberately sickening the populace and denying them the use of the wells. Since the horrific events of Sep. 11, 2001, Anthrax again surfaced as a threat when a nameless, faceless terrorist used the U.S. Postal Service to deliver biological weapons in the form of letters to senior Government officials and the press.

Despite a history of armies poisoning rival water supplies, institutional dogma has generally downplayed the risk of asymmetric chemical and biological attacks on water. Nationally recognized as critical infrastructures, water systems are vulnerable to disabling attacks. At present, most governments and their relevant agencies lack comprehensive or robust remediation and counter terrorism processes to address this great potential threat.

The nation's water infrastructure is impossible to fully secure. The sheer vastness of the system with its "raw water" reservoirs and tens of thousands of miles of exposed aqueducts and pipeline with little or minimal security, make it logically and fiscally impossible to completely police. The nation's water system is a delicate balance of interlocking components that includes: the water supply system (dams, reservoirs, wells, etc.); water treatment system; and the water distribution system (pipes, pumps storage tanks, etc.). These systems are mostly aging and in urgent need of upgrading, not simply to bolster them from terrorist attack but to keep them adequately handling the growing water needs of the 21st Century.

Raw water is generally treated at the treatment plant to meet federal, state standards, or Department of Defense (for overseas fixed installations) guidelines and to improve its taste and corrosion characteristics. To meet standards, contaminants must be removed or neutralized. Treatment requirements vary greatly depending on raw water quality and community population (these factors affect which standards apply). A small system supplied by a secure well might only require simple chlorination. Larger systems with surface sources have multiple filtration, physical/chemical modification and disinfection units. Common in the U.S., but typically not used in Europe, chlorine disinfectant is added to kill microbial contamination and residual chlorine is maintained to control microbial life within the system. Examples of other chemical addition are precipitation of iron or other metals, reduction of the water's corrositivity and adding fluoride for children. Upon treatment, the water is considered potable or safe to drink.

By its very nature a treatment plant provides both security from and facilitates chemical or biological attack. Treatment processes may very well remove/neutralize an agent introduced into the raw water or local system. On the other hand, it is the controlling point for system quality where chemicals are deliberately and systematically added to the water. The plant lends itself as an ideal attack point for water downstream in the system. Therefore, treatment plants are potential critical points of a water distribution system.

Two particular points in the water system are also of particular vulnerability and could provide harmful effectiveness to terrorists; water intakes and water distribution:

Water intakes: The potential for contamination increases as water dilution decreases, and such is the case for water intakes. There are 6,800 public supply drinking water intakes on rivers alone in the U.S. Likewise; intakes at the mouths of reservoirs or lakes are also vulnerable targets. Contaminates introduced at the intakes have a far better chance of reaching the population than if introduced elsewhere.

Water distribution: This component of the water supply is the most vulnerable. Pipelines wander for thousands of unprotected miles; aqueducts snake through largely unpopulated areas. A person with a crude knowledge of hydraulics and a bicycle tire pump and access to a kitchen faucet could introduce toxins into any local water distribution system, thus endangering thousands. There are few robust security methods in place to protect these distribution systems.

The distribution system is an underground network of iron, concrete or PVC (plastic) pipes that transport the treated water under pressure to the consumers. Ultimately, water is plumbed into each building from these underground mains. High pressure makes it difficult, though not impossible, to inject material into the typically buried lines. A distribution system typically has a variety of valve pits and other control points where maintenance personnel, or an adversary, may gain access to the water.

Though relatively secure, the system pipes and valves are critical points. Any adversary with access to basic chemical, petrochemical, pharmaceutical, biotechnological or related industry can produce biological or chemical (e.g., "bio-chem") weapons into water supply systems. Compared to aerial attack (inhalation or skin contact), effective doses are easier to obtain in water (less dilution than air and directly ingested by the target), and in many cases the materials are more stable (protected from ultraviolet and temperature extremes, although exposed to chlorine). To effectively kill or disable from drinking water chemical and biological agents must be:

1.—Weaponized, meaning it can be produced and disseminated in large enough quantities to cause desired effect.

2.—A viable water threat, meaning it is infectious or toxic from drinking water.

3.—Stable, meaning the agent maintains its structural and virulent effects in water.

4.—Chlorine resistant, meaning the agent isn't significantly oxidized by free available chlorine (FAC) present in most American water systems. Chlorine susceptibility can be negated by inactivation of system chlorination devices.

There are two types of biological threats, pathogens and toxins. Pathogens are live organisms, such as bacteria, viruses or protozoa, which infect and cause illness and/or death. The other are: biological toxins, chemicals derived from organisms, primarily bacteria and fungi, which cause chemical toxicity resulting in illness and/or death. It is believed that for less than $10,000, anyone with gear no more sophisticated than a home brewing kit, protein cultures and personal protection can cultivate trillions of bacteria with relatively little personal risk.

Mankind wages a constant battle against pathogens. Bacteria, viruses, protozoa, nematodes fungi, and others are the causes of most infectious diseases. Living organisms, they require a host population and certain environmental conditions (temperature, humidity/water, and protection from sunlight) for survival. Upon infection, the pathogen must "grow" in the host. This latency period requires time, depending on the organism, from hours to weeks.

The medical profession, and in particular the dental industry and the medical research community, are taking steps to improve the quality of water used in patient care. Dental unit waterlines (the tubes that connect the high-speed handpiece, air/water syringe and ultrasonic scaler to the water supply) have been shown to harbor a wide variety of microorganisms including bacteria, fungi, and protozoans. These microorganisms colonize and replicate on the interior surfaces of the waterline tubing, inevitably resulting in adherent heterogeneous microbial accumulations termed "biofilms." Biofilms, once formed, serve as a reservoir significantly amplifying the numbers of free-floating microorganisms in water exiting the waterlines. Dental unit water systems currently designed for general dental practice are incapable of efficiently and/or effectively delivering water of an optimal microbiologic quality.

Filters may physically stop particles and contaminants from progressing through liquid treatment system, but are less effectiveness in preventing microorganisms from flowing to the liquids eventual use because microorganisms such as bacteria, viruses and protozoa's are capable of developing within filters and fluid passages (e.g., waterlines an air ducts), leaving the liquid treatment system less effective. Furthermore, overuse or failure of a filter can lead to even higher levels of microorganisms flowing to end user than if the filters were not used at all. To date, however, there is insufficient data to establish the effectiveness of available liquid sterilization methods. Most systems and methods of cleansing water and air supplies do not directly address microorganism buildup that may occur within waterlines and air ducts throughout the day. A wider range of alternatives and adjuncts to the above listed options is desirable. It is further desirable that treatment of fluid that might be carrying harmful microorganisms will occur at a point closest to the "point of use" for the fluid in order to ensure a higher probability of treatment system effectiveness.

Chemical approaches to disinfecting dental unit water lines have enjoyed varying success. One approach is the use of iodine to disinfect waterlines. The safety and efficacy of chemical disinfection protocols have not been sufficiently validated in the past; therefore the Council has strongly discouraged dentists from treating their dental unit waterlines chemically. In particular, the Council has warned against the use of glutaraldehyde in treatment-water delivery systems to meet the goals set out in the ADA's Statement on Dental Unit Waterlines. Glutaraldehyde is a recognized health hazard; it is a known dermal, mucosal, respiratory and systemic irritant that, as stated on its labeling, is only intended for use in closed containers. In addition to the potentially serious adverse health effects that may be associated with glutaraldehyde when used in dental unit waterlines, such use will essentially fix or "glue" the biofilm matrix to the surface of the waterline, leaving an ideal environment for microbial re-colonization.

To date, however, there is insufficient data to establish the effectiveness of available water and air sterilization/purification methods. Many of the described methods do not directly address microorganism buildup that may occur within waterlines and air ducts throughout the day. It is further desirable that treatment of fluid in tubing (e.g., waterlines, air ducts) occur at a point closest to the "point of use" in order to ensure a higher probability of treatment system effectiveness.

SUMMARY OF THE INVENTION

The present inventors have found that light can be a solution to countering biological and/or chemical ("bio-chem") terrorism and also propose systems for killing or disabling the harmful effects of some microorganisms. Light at a certain wavelength can excite a catalyst to create hydroxyl radicals, which can sort of perform as bullets for microorganisms. These powerful oxidizing agents break the toughest chemical bonds, and convert biological agents into carbon dioxide and water. The present inventors propose the use of laser-generated radiation (e.g., illumination at certain wavelengths) to render microorganisms un-ineffective (a technical "kill" that reduces the infectivity of microorganisms). In accordance with the present invention, a light source illuminating at particular ultraviolet wavelengths into fluid treatment areas can be effective in disabling the DNA of harmful microorganisms.

A basic system of the present invention will include a treatment area, which can be presented in the form of a fluidtight (e.g., gas-tight, liquid-tight) junction box having an entry point for receiving fluid (e.g., air, water, blood) from input tubing connected to the input portion of the junction box and an exit point for to allow treated fluid to continue moving towards its point of use. At least one laser light source is coupled to the junction box. The laser light source can be provided in the form of at least one fiber optic line coupled to a laser and also coupled to the junction box, or as at least one laser directly coupled to the junction box, at one or several points about the junction box for delivery of light from laser(s) into the treatment area and onto microorganisms carried by fluid.

The junction box can comprise of a stainless steel, watertight/airtight housing. The internal surfaces of the housing can be highly polished to allow for reflection of light. Reflectors, deflectors and/or diffuser can be included within the housing to scatter light. Baffles, walls or spiraled tubing can be formed within the housing in order to create flow channels throughout the housing, thereby providing more opportunities for light treatment. The baffles or walls can provide for a serpentine configuration of flow chambers within the housing. Laser UV light sources can be provided for/within each chamber of the serpentine configuration. When more than one laser is used, each laser can be tuned to (or selected to perform at) a unique wavelength.

A flow sensor can be provided to turn on the laser light source(s) whenever flow through the junction box is sensed. A microorganism detector can be included near the entry point to detect the presence of harmful microorganism. A control means responsive to the detector and/or the flow sensor can turn on the laser light source(s) in response to an indication of either or both flow and/or microorganism detection. Furthermore, a variable wavelength controller can be provided to adjust the wavelength of light produced by laser light source(s). Adjustment to the illumination/wavelength of laser light sources(s) can be in response to said detector, thereby enabling for precise targeting of detected microorganisms.

A filtration capability can be included near or before the entry point of the treatment area. Filtration can reduce or eliminate particles from fluids prior to laser treatment. Particles can cause light to be absorbed or scattered, thereby reducing the effectiveness of laser treatment, therefore filtration prior to laser treatment is preferred. Filtration can also be provided after treatment, thereby removing additional particulates and/or killed microorganisms.

Treatment systems can be staged as part of a larger system, providing for a system comprising more than one treatment area and associated laser light sources that are coupled, one after the other. Such staging can provide for concentrated redundancy prior to delivery of fluid to its point of use. Treatment systems can include means to detect and/or analyze microorganisms and/or chemicals within a fluid distribution system. For example, detection and/or analysis systems can be deployed at various stages along a water distribution system, near, or as part of, a treatment system, thereby allowing for protection (e.g., detection, treatment) redundancy. Also, detectors can be located at intakes of a heating and air conditioning system for buildings, airplanes, and other controlled environments, to detect microorganism/chemicals within the air of an environment. UV light treatment units can be deployed throughout both water and air systems to illuminate the fluid and target the detected microorganisms.

The treatment systems, including detection/analysis means, can be networked to a remote monitoring (e.g., command and control units) through wired and/or wireless networking and communication systems. Networked monitoring and assessment can enable rapid deployment of counter measures within affected fluid (water/air) distribution systems and populated communities, to include emergency shut-off of control valves that can be associated with the present systems.

DESCRIPTION OF THE DRAWINGS

The novel features believed characteristic of this invention are set forth in the appended claims. The invention itself, however, as well as a preferred mode of use, further objects, and advantages thereof, will best be understood by reference to the following detailed description of an illustrative embodiment when read in conjunction with the accompanying drawings, wherein:

DETAILED DESCRIPTION OF THE INVENTION

The following description is presented to enable persons skilled in the art to make and use the invention, and is provided in the context of particular applications and its requirements. Various modifications to the disclosed embodiments will be readily apparent to those skilled in the art, and the general principles defined herein may be applied to other embodiments and applications without departing from the spirit and scope of the present invention.

Thus, the present invention is not intended to be limited to the embodiments shown, but is to be accorded the widest scope consistent with principles and features disclosed herein. Although preferred embodiments of the present invention are described herein, those skilled in the art can appreciate that a number of varying embodiments may be implemented in accordance with the present invention.

The following U.S. Patents and Application documents are incorporated herein by reference for their teachings:

U.S. Pat. No. 5,948,272 entitled "SYSTEM AND METHOD FOR DETECTING AND NEUTRALIZING MICROORGANISMS IN A FLUID USING A LASER" and issued to Lemelson on Sep. 7, 1999;

U.S. Pat. No. 5,809,185 entitled "SENSOR FOR DETECTING MICROORGANISMS" and issued to Mitchell on Sep. 15, 1998;

U.S. Patent Application No. 2001/0049464A1 entitled "THERAPEUTIC METHOD AND APPARATUS FOR DEBILITATING OR KILLING MICROORGANISMS WITHIN THE BODY" by Ganz, published Dec. 6, 2001; and U.S. Patent Application No. 2002/0014461A1 entitled "POINT-OF-USE WATER TREATMENT SYSTEM" by Kuennen et al., published Feb. 7, 2002.

Ultraviolet sterilization is one proven method of eliminating a variety of harmful waterborne microorganisms. Short-wave ultraviolet light (e.g., between 200–300 nm) technically "kills" (e.g., renders them un-infective) microorganisms with ease, providing they are exposed to the radiation for a sufficient length of time. The UV light breaks the "DNA chain" thus preventing the microorganism from reproducing. All UV sterilizers are generally provided as a hollow chamber containing an appropriately sized cylindrical UV bulb. Fluid (water/air/blood) enters the chamber at the sterilizer inlets, circulates within it for the proper length of time (dwell time) to ensure a high kill rate and returns to the tank via the sterilizer outlet. For maximum benefit, UV sterilizer must generally be run on a continuous 24 hour-per-day basis. UV sterilizers are also highly effective at controlling algae blooms in both marine and freshwater aquaria.

The portion of the UV light spectrum known to affect living organisms ranges in wavelengths from 190 nm to 400 nm and is divided into 3 bands: UVa, UVb, and UVc. The UVc light band of from usually about 200 nm to 290 nm is often referred to as the germicidal band. UVa and UVb light bands are not useful for water sterilization. Many factors, however, affect the overall effectiveness of UV sterilization: the size of the organism may affect the effectiveness of ultraviolet sterilization (the larger the organism the greater the dosage of UVc light required); UV power (the lamp wattage required for sterilization is related to flow rate of water through the UV sterilizer); contact time (determined by the flow rate of the water through the UV sterilizer, very critical); temperature; and the use of quartz sleeves with UV lamps (the amount of UVc output of the UV lamp dependent on the temperature at which it operates.

After the introduction of the ruby laser in 1960, lasers have become widely used in medicine and dentistry for soft tissue surgical procedures and more specifically the CO2 and Nd:YAG lasers for oral soft tissues surgery. Both of these lasers have FDA approval for this function. In the enhancement of a chemical curettage with a laser, the Nd:YAG is ideal because of its use of an optical fiber for the transmittal of the laser energy into the gingival sulcus. Not all lasers are the same. The difference between them is primarily dependent upon their wavelength. Each laser produces light at a different wavelength with a different intensity in a very specific time period. Wavelength affects both the clinical applications and design of the laser. The wavelength of lasers used in medicine and dentistry generally range from 193 to 348 nanometers to 10,600 nanometers.

Advances in semiconductor lasers (e.g., VCSELS, vertical cavity surface emitting lasers, diodes) are also a source for the delivery of ultraviolet light at wavelengths appropriate for fluid treatment in accordance with the present invention.

Figure 1:
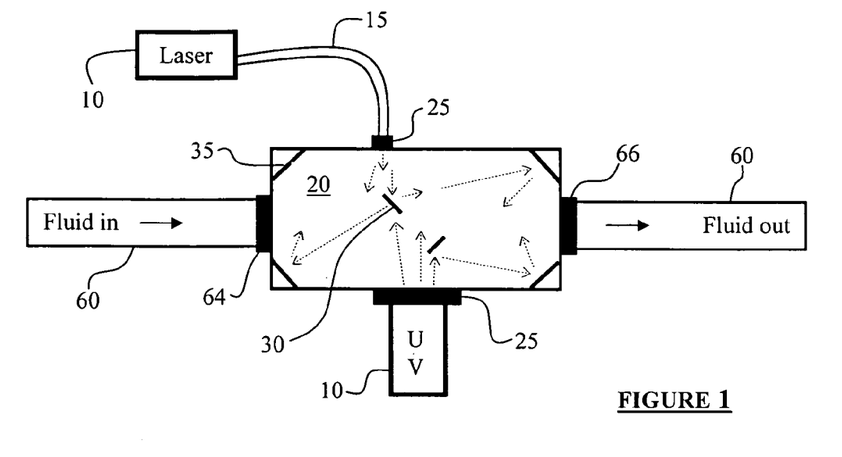
FIG. 1 is as illustration of a laser fluid treatment system in accordance with one embodiment of the present invention.

Referring to FIG. 1, the light source can be provided in the form of a fiber optic cable 15 that extends from a light source 10 to a treatment area 20, so as to carry light from the source 10 through a coupling 25 into the treatment area 20. Light deflectors 30, reflectors 35 or diffusers, e.g., of conical shape, inside the treatment area 20, can be used to spread and/or scatter light rays (shown as dashed arrows) throughout the treatment area 20 so that the light rays can interfere with microorganism contained within fluid passing through the treatment area 20. Reflector/deflector surfaces to enable effective light scatter are known in the optical arts. Fluid is carried to the treatment area 20 from a supply line 60. The supply line is coupled to an input port 64 at the treatment area 20. The supply line 60 is again coupled to the treatment area 20 at an exit port 66. It should be appreciated that the treatment area 20 as shown in the drawing can be a self-contained unit that is spliced into an existing fluid line 60. The treatment area is preferably fluidtight (e.g., gas-tight, liquid-tight) so prevent leakage.

The light source 10 can be comprised of any suitable commercially available lighting source useful for emitting light at wavelengths necessary for destroying microorganisms, e.g., a mercury vapor lamp or laser for providing UV radiation. Depending on its environmental application (e.g., constructive limitations of the housing for the treatment area), a laser would preferably be operated intermittently and on low power to the extent the system is enabling the killing or disablement of microorganisms without damaging treatment equipment. But it should be appreciated that lasers or light sources at very high power can also be used depending on the durability of housing materials).

Figure 2:
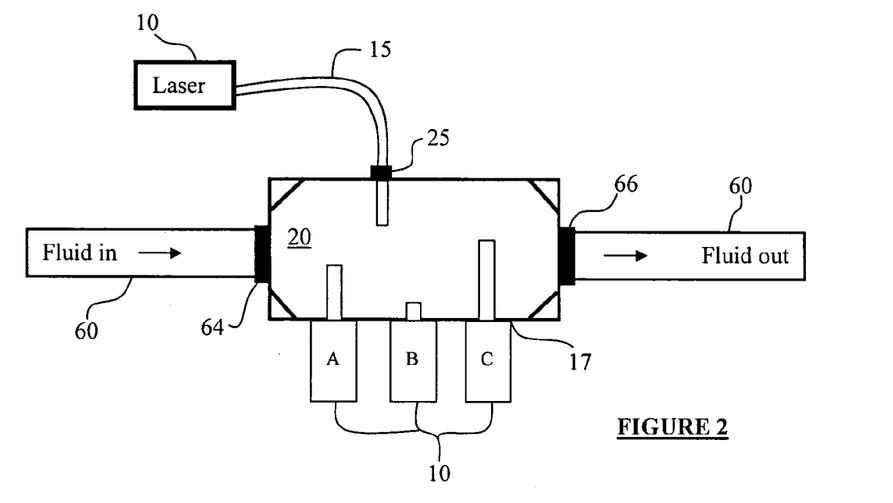
FIG. 2 is an illustration of a laser fluid treatment system including laser light source depth deployments in accordance with another embodiment of the present invention.

The treatment area and laser configuration can take many forms in order to increase exposure time and laser redundancy. Referring to FIG. 2, a treatment area 20 is shown wherein more than one laser 10 is coupled to the housing of the treatment area 20. Coupling 25 can be directly 17 or by fiber optic 15. Also shown is the placement of laser sources at various depths A, B and C within the treatment area 20. Light sources at various depths within a treatment area will increase exposure and intensity throughout a treatment area. A laser beam is effective to finite depths depending on laser power and fluid clarity; therefore many light sources at various depths can overcome loss of laser effectiveness due to beam scatter/diffraction within the treatment area 20. Again, optical reflectors, deflectors and/or diffusers can be used in combination with laser source depth to provide effective fluorescence within the treatment area and about the fluid contained therein.

Figure 3:
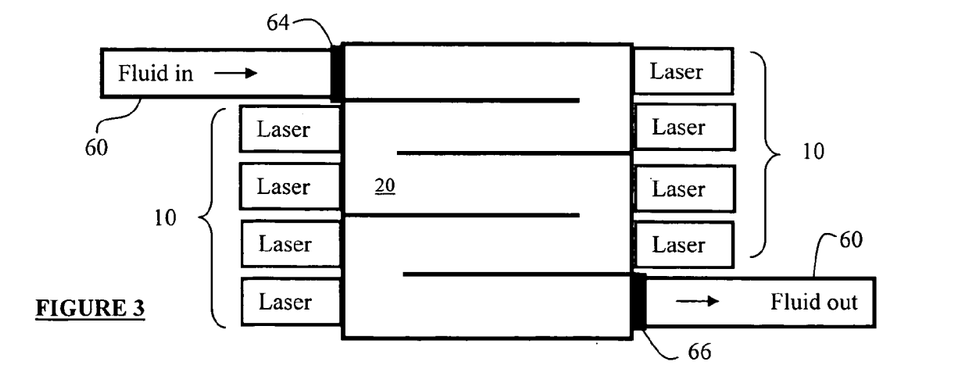
FIG. 3 is as illustration of a laser fluid treatment system including a serpentine-like configuration in accordance with yet another embodiment of the present invention.

Another proposed treatment area design is provided in a serpentine configuration. As seen in FIG. 3, fluid entering the treatment area 20 from the tubing 60 at coupling 64 is carried through the treatment area 20 in a serpentine flow pattern because of various partitions 70 built into the treatment area 20. Although four compartments are shown in the illustration, it should be appreciated that more or less compartment can be provided for fluid flow and light exposure. Furthermore, it should be appreciated that internal surfaces can be rounded, smooth and/or polished in order to promote ease of fluid flow and maximum light exposure, yet reducing flow restriction. Lasers 10, or fibers, can be coupled to the housing at throughout the various compartments formed by the partitions.

The serpentine configuration increases exposure because of the increased number of light sources 10 coupled to the housing and also because of the added length and volume created by the compartments. Exposure time of microorganisms to radiation is generally increased because the serpentine flow pattern creates length to the flow of fluid.

Figure 4:
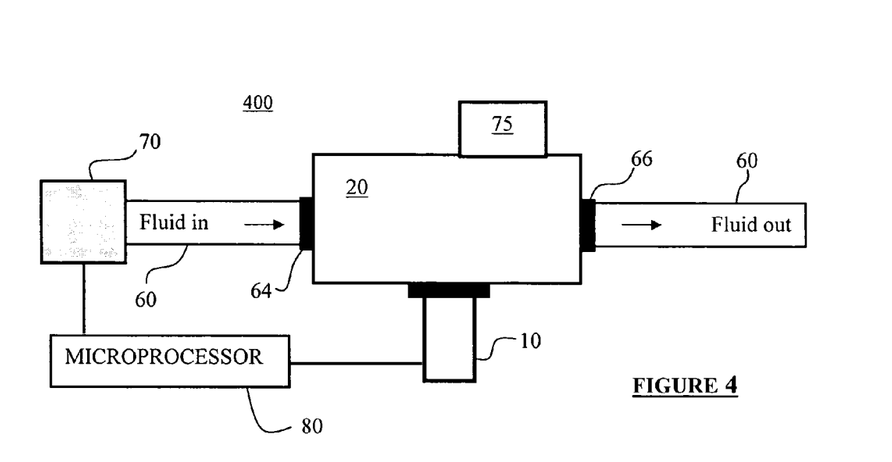
FIG. 4 is an illustration of a laser fluid detection and treatment system including sensors and a microprocessor in accordance with the present invention.

Referring to FIG. 4, another embodiment of the present invention is illustrated. The system 400 can include a microorganism sensor 70 is deployed near the entry point 64 to the treatment area 20. The sensor 70 can be coupled to a microprocessor 80 (e.g., computer) where sensor input is analyzed to determine if targeted harmful microorganisms exist in fluid flowing through the pipeline 60. If microorganisms are detected, the microprocessor can control the illumination by light sources 10. The microprocessor can also control the wavelength the light sources illuminate at where it is determined that a particular wavelength of light is most effective against a detected microorganism. The microprocessor can also control more than one light source 10 independently.

A flow sensor 75 can also be provided as part of the system 400 in addition to, or instead of, the microorganism sensor 70. The flow sensor 75 can sense if fluid is flowing through the treatment area, and in response can turn on the light source(s) 10. It should be appreciated that the flow sensor 75 can be located either at the entry point 64, exit point 66 or within the treatment area 20. Use of the flow sensor 75 will control the amount of time that light sources are turned on. The light sources 10 can turn off when flow is no longer sensed, or after a set time period in which case a timer. Timing can be provided by a microprocessor 80 for each light source 10.

Figure 5:
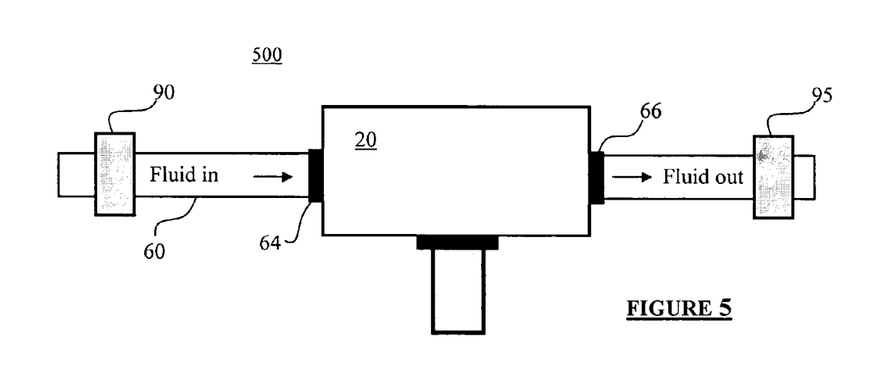
FIG. 5 is as illustration of a laser fluid treatment system including filtration in accordance with another embodiment of the present invention.

Referring to FIG. 5, a system 500 is shown wherein filtration 90 is incorporated along pipeline 60 before the entry point 64 of the treatment area 20. A filter can remove particles, which would interfere with or absorb the light intended for fluid treatment. It should be appreciated that a filter 95 could also be provided along pipeline 60 after the treatment area and exit point 66.

Figure 6:
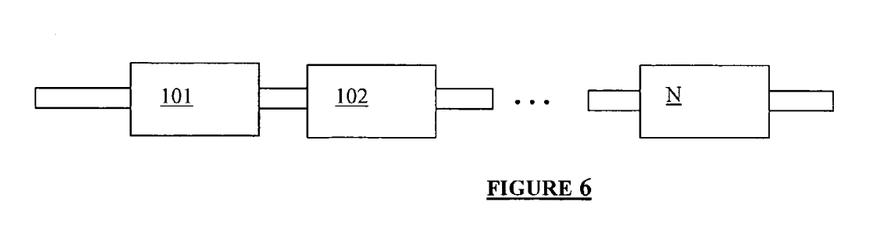
FIG. 6 is an illustration of a laser fluid detection and treatment system included stages of more than one system in accordance with another embodiment of the present invention.

Referring to FIG. 6, more than one system can be provided in stages in order to maximize treatment success. As shown in FIG. 6, a first treatment system 101 is coupled to a second treatment system 102. Subsequent treatment systems N can be further coupled in line with a prior treatment system. It should be appreciated that each stage (e.g., .101, 102 . . . N) can be tasked to target (e.g., detect and/or impede) the same microorganisms, or can be assigned specific targets and wavelengths.

Figure 7:
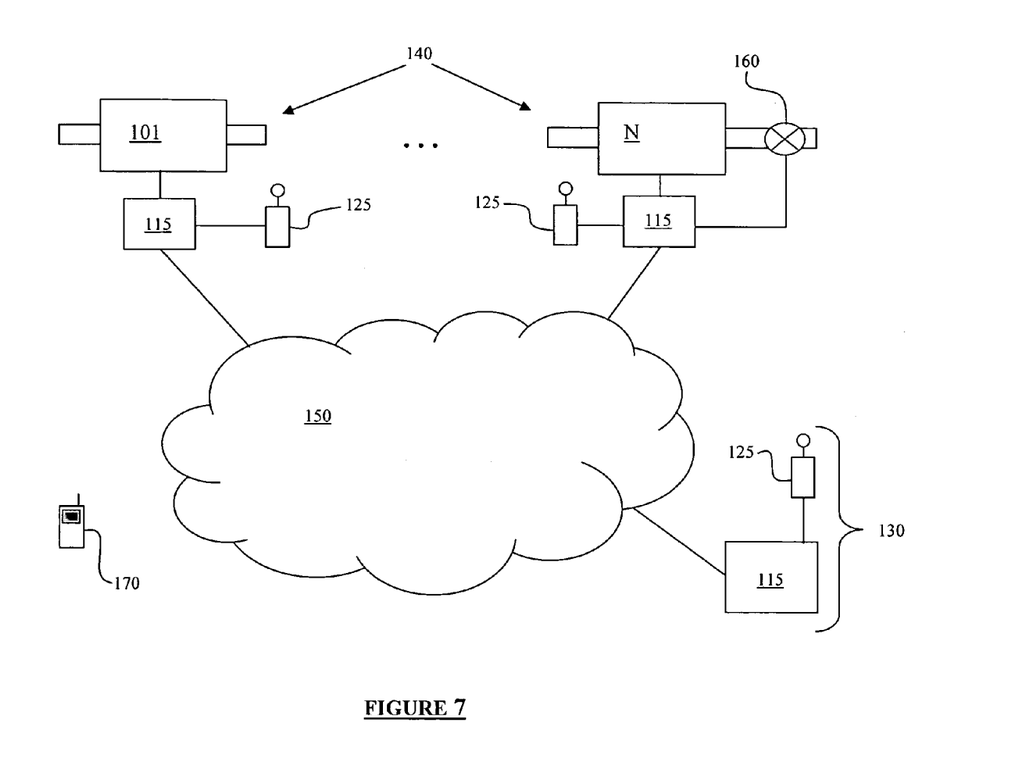
FIG. 7 is an illustration of laser fluid detection and treatment systems in communication with remote monitoring and control agencies in accordance with another embodiment of the present invention.

Referring to FIG. 7, detection and/or treatment systems 101 can communicate with remote monitoring and control agencies 130 through communication means known in the art. Network 150 communications can be wired and wireless, public and private, secured and unsecured. The field of communications is well developed, therefore it should be appreciated to those skilled in the art that wired 115 and wireless 125 communication equipment can be used to provide at least one of detection, analysis and/or treatment information to remote agencies 130. For example, public wireless network 150 generally communicate using standards and networks such as, among others, 3G, WAP, CDMA, TDMA, GPRS and CPDP. These standards can be used to provide communications between deployed systems (101 through N) at nodes along a fluid distribution network 140 and responsible monitoring agencies 130 operated by Government and private concerns.

For example, when a biological or chemical agent is detected at system 101, then emergency shut-off procedures can be initiated by the agency 130 to a remote valve 160 that is located safely downstream from the harmful agent. It should be appreciated that monitoring and control can be carried out by a central computing system, thereby providing for automated command and control. It should also be appreciated that a command and control agency 130 can also utilize the assets of a computer to analyze the threat and suggest, or automatically initiate, valve shut-off for several valves deployed throughout the fluid distribution system (thereby effectively shutting down and isolating the potential threat).

Also, Internet Packet (IP) protocol communication is well known in the data communications art. Therefore, the skilled should appreciate that systems and controllers 130 can communicate status and functions through data networks 150 (e.g., the Internet or private data networks). It should further be appreciated that a hybrid of communications, or communication redundancy, can be provided at each node in an entire system in order to ensure communication is sustained. As broadband communications assets continue to be deployed (e.g., WiFi and Bluetooth communications), it should be appreciated that components within a larger system can communicate status and render command remotely.

Furthermore, it should be appreciated that systems and components deployed throughout fluid distribution systems can be monitored by personnel in the field using portable wireless devices 170, such as laptops, PDAs (personal digital assistants), Smartphones, and other handheld wireless data-, and network-enabled devices that can be deployed in a field environment.

Figure 8A:
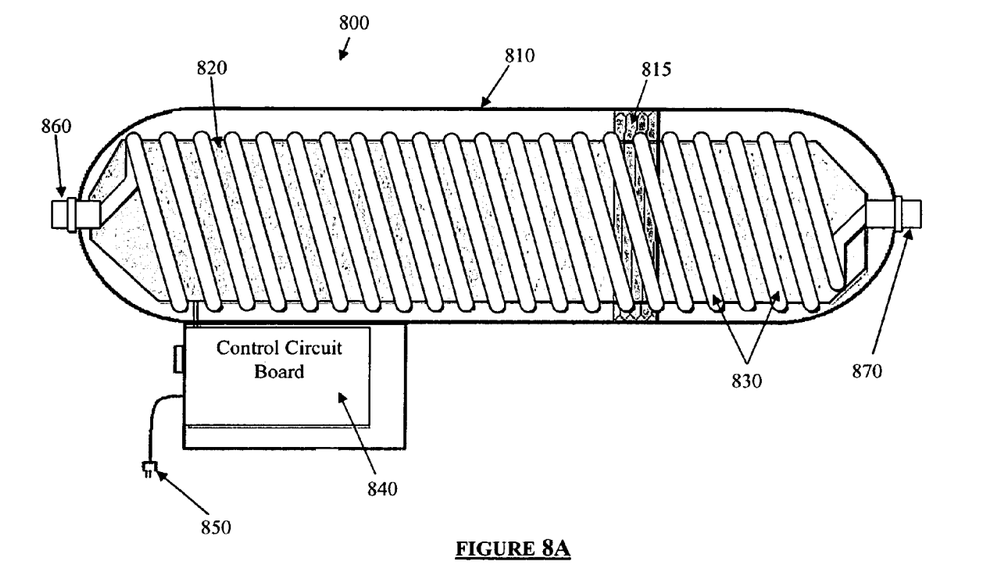
FIG. 8A is as illustration of a fluid treatment system in accordance with another embodiment of the present invention wherein fluid is routed through a spiraled UV transparent tubing surrounding UV light sources contained within a protective housing.

Referring to FIG. 8A, an alternative fluid treatment system 800 is illustrated. The system 800 depicted is scalable (as are the previously described system) to take the form of a portable, battery operated system for use in the field (e.g., military, recreational) or as an under counter treatment system for water fountains, sinks, portable water supplies, medical water supplied, etc, or as larger units for use in-line in air and water distributions systems associated with a facility. The treatment system 800 includes a housing 810 containing a spiraled, transparent fluid carrying medium 830 which is spiraled in such a manner that it surrounds a UV light source 820 located within the middle of the housing and fluid carrying medium 830. A fluid input connection 860 allows fluid to enter the treatment system housing 810 through the fluid carrying medium 830 and exit through a fluid output connection 870 after UV light treatment. A circuit board 840 can control the UV light source 820, which can take the from of several semiconductor laser or diodes disposed on a circuit board. The power source 850 can be AC (120v) or DC where portability is required. Power sources can include batteries, solar cells or generators. The fluid input connection 860 and output connection 870 can be in the form of threaded fittings or detent connections that are familiar with their use in air compressors.

Figure 8B:
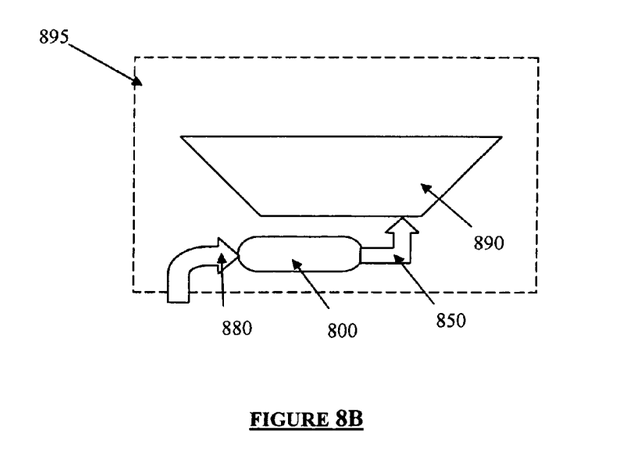
FIG. 8B is an illustration of the fluid treatment system of FIG. 8A deployed in an environment requiring fluid treatment in accordance with various fields of use and applications of the present invention.

Referring to FIG. 8B, the fluid treatment system 800 is illustrated as it can be deployed within a fluid delivery system 895. The fluid delivery system 895 will generally include fluid input tubing 880 that is connected to the fluid input connection 860, and fluid output tubing 850 connected to the fluid output connection 870. The point of use 890 may take the form of water or air delivery means familiar to facilities (e.g., water faucets, air ducts) and modes of transportation (air recirculation systems in airplanes).

Figure 9A:
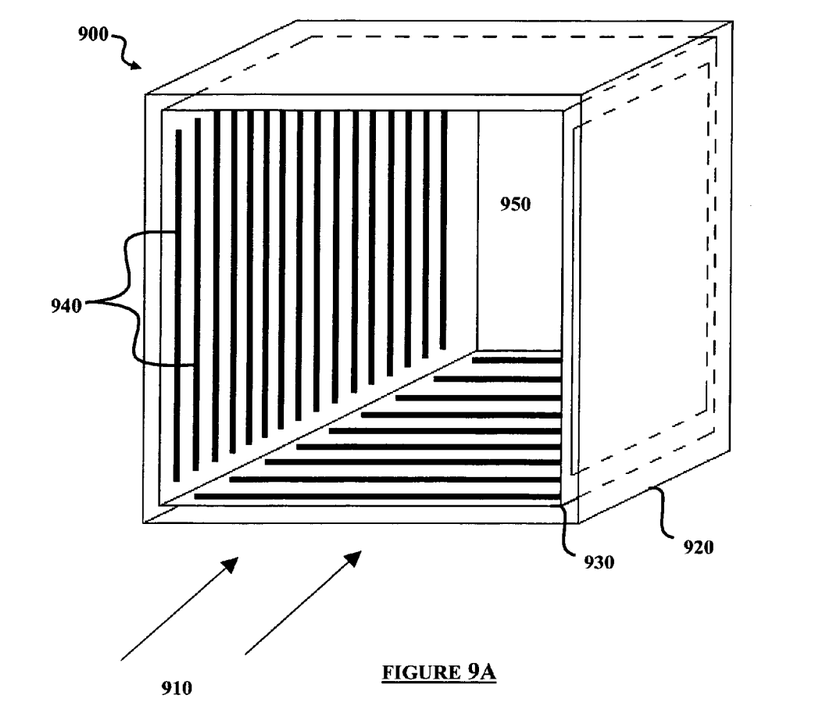
FIG. 9A is as illustration of a laser fluid treatment system including a plenum lined with UV light sources and adapted for deployment along a fluid delivery system configuration in accordance with yet another embodiment of the present invention.

Referring to FIG. 9A, an air treatment system 900 is shown. As intake air flow 910 is drawn thru the inner plenum 920, typically via fans or any other means, UV-emitting semiconductors (e.g., VCSELS/diodes) are formed in a UV array 940, the UV array 940 representing in the drawing representing a combination of circuit boards and UV-emitting semiconductors. The UV arrays 940 are contained along the walls of the inner plenum 920 such that the inner plenum does not block UV light from emitting towards the treatment area located within the center of the system 900. Entering Air flow 910 is sterilized as it passes thru the inner plenum 920 and then exits as treated air flow 950 exits from the system 900. The back side of the inner plenum 920 contains the circuit board(s) 930 that the UV-emitting semiconductors 940 are attached to. The circuit boards 930 are energized by an external power source (not shown) and the UV laser diodes can be continuously energized while air is flowing through the inner plenum 920. The inner plenum 920 sits within an outer plenum which provides strength, support, and rigidity to the system 900. Ideally, the circuit board(s) 930 are capable of being replaced in the event of a failure of the board or more than acceptable number of UV-emitting semiconductors. The UV emitting semiconductors and arrays 940 should not be connected in series circuits in order to prevent large blackouts areas within the treatment area. The inner plenum can be perforated with holes or contain slits that enable the UV-emitting semiconductors to direct light towards the general flow of air. It should be appreciated that the outer plenum can be flanged to allow for the unit to be inserted into any airflow stream. The system 900 will preferably be easily removed to allow maintenance and cleaning.

Figure 9B:
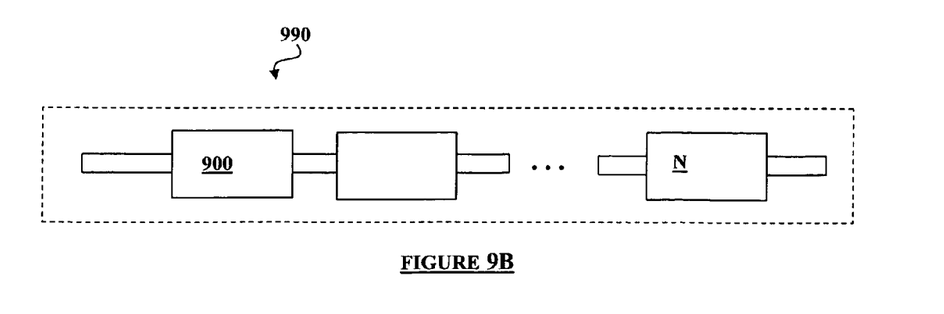
FIG. 9B is an illustration of the fluid treatment system of FIG. 9A deployed in an environment requiring fluid treatment in accordance with various fields of use and applications of the present invention.

Referring to FIG. 9B, the treatment system 900 of FIG. 9A is illustrated as it can be deployed within a larger fluid delivery/distribution system 990. The fluid delivery system 900 can be connected at several location along air distribution tubing (e.g., air passages) servicing a controlled environment. As shown in the drawing, several stages "N" can be incorporated along an air delivery system for better UV coverage of the fluid It should be appreciated that the system 900 can be adapted for use in most air delivery systems familiar to facilities (e.g., water faucets, air ducts) and modes of transportation (air recirculation systems in airplanes).

Figure 10A:
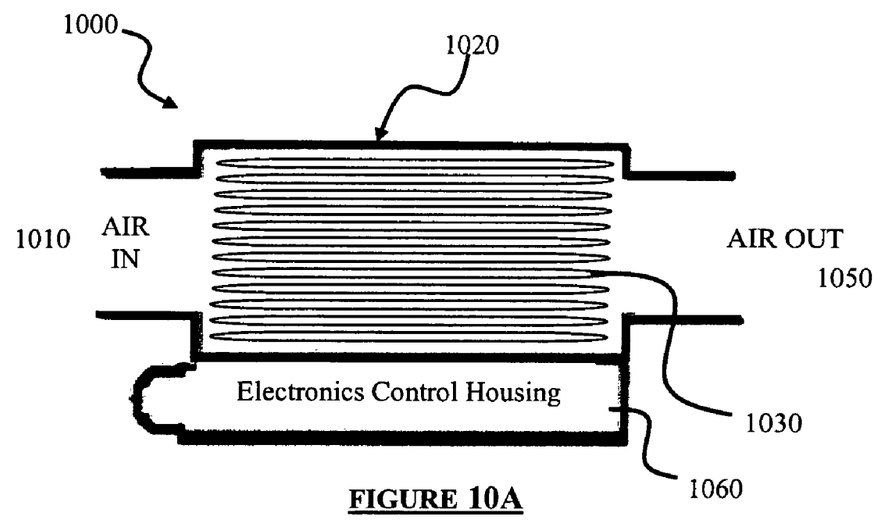
FIG. 10A is as illustration of yet another laser fluid treatment system including a plenum lined with UV light sources disposed and adapted for deployment along a fluid delivery system configuration in accordance with yet another embodiment of the present invention.
Figure 10B:
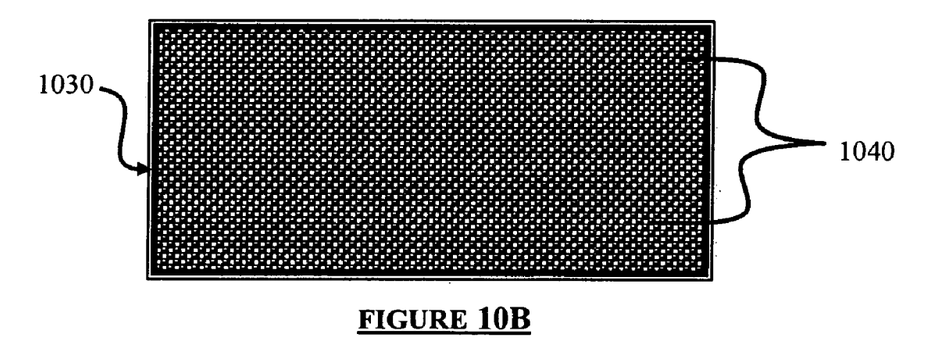
FIG. 10B is an illustration of the fluid treatment system of FIG. 10A deployed in an environment requiring fluid treatment in accordance with various fields of use and applications of the present invention.

Referring to FIG. 10A, another embodiment of an air treatment system 1000 is shown. Like the system described in FIG. 9A, intake air flow 1010 is drawn through an inner plenum 1020, typically via fans or any other means. UV-emitting semiconductors (e.g., VCSELS/diodes) are disposed within the plenum 1020, thereby forming a UV treatment area for air. In this system, several UV arrays 1030 are disposed throughout the treatment area, which provides for more direct and intense UV coverage over the in-flowing air 1010. As shown in FIG. 10B, it should be appreciated that the UV arrays can be provided in the form of circuit boards 1030 having a plurality of UV-emitting semiconductors 1040 formed there on each side of the circuit board 1030. It should also be appreciated that the circuit boards could be disposed as an array within the housing at a ninety degree angle to the incoming air flow 1010, which would thereby provide a series of baffles that air must move through during treatment. For example, one skilled in the art can appreciate that the arrays 1030 can be arranges within the housing to cause formation of a series of channel in a serpentine configuration similar to that shown in FIG. 3, which would thereby cause the air to be exposed to UV light for a longer duration of time without causing too much of an impediment to the air flow through the plenum 1020.

U.S. Pat. No. 5,948,272 entitled "SYSTEM AND METHOD FOR DETECTING AND NEUTRALIZING MICROORGANISMS IN A FLUID USING A LASER" and issued to Lemelson on Sep. 7, 1999 and U.S. Patent Application No. 2001/0049464A1 entitled "THERAPEUTIC METHOD AND APPARATUS FOR DEBILITATING OR KILLING MICROORGANISMS WITHIN THE BODY" by Ganz, published Dec. 6, 2001 describe systems that can be used in medical application to treat ailment in the human body. It should be appreciated that the present invention can be used for medical applications for the human body. For example, blood containing harmful biological organisms can be cycled through the systems described herein and in particular in FIGS. 3 and 8A, in order to expose a targeted microorganism to UV light. A patient could be placed in fluid connection to the present systems similar to treatment methods utilized for kidney dialysis and photoluminescence procedures/treatment for blood disorders and illness.

The embodiments and examples set forth herein are presented in order to best explain the present invention and its practical application and to thereby enable those skilled in the art to make and utilize the invention. Those skilled in the art, however, will recognize that the foregoing description and examples have been presented for the purpose of illustration and example only. The description as set forth is not intended to be exhaustive or to limit the invention to the precise form disclosed. Many modifications and variations are possible in light of the above teaching without departing from the spirit and scope of the following claims.

We claimed:

1. A fluid-borne hazard detection and fluid treatment system, comprising:
    at least one detector deployed at nodes along a fluid distribution system for detection biological microorganisms and/or chemicals;
    communications system deployed with said detectors at the nodes for reporting detection of the biological microorganisms or the chemical to remote monitoring systems and for receiving treatment commands from said remote monitoring systems; and
    treatment areas deployed at said nodes for providing ultraviolet light into fluid containing said biological microorganisms, said treatment areas further comprising a housing having an entry point for receiving fluid into said treatment area and an exit point for allowing treated fluid to continue moving towards its point of use and at least one ultraviolet semiconductor laser light source coupled to the housing, said treatment area for providing ultraviolet light into fluid containing biological microorganisms.

2. The invention of claim 1, further comprising flow sensors deployed at said nodes, wherein said sensors turn on the ultraviolet laser light sources whenever flow through nodes is sensed.

3. The invention of claim 1, further comprising at least one shut-off valve deployed at said nodes, said at least one shut-off valve responsive to at least one of said detectors or said remote monitoring systems by blocking fluid flow through said nodes.

4. The invention of claim 1 wherein said housing is fluidtight and comprised of stainless steel internal surfaces that are highly polished.

5. The invention of claim 1, further comprising a variable wavelength controller can be provided to adjust the wavelength of light produced by the ultraviolet laser light source in response to detection by said at least one detector.

6. The invention of claim 1, further comprising a flow sensor wherein said flow sensor can cause said at least one ultraviolet laser light source to be turned on whenever fluid flow through said treatment area is sensed.

7. The invention of claim 1, further comprising at least one filter deployed near at least one of said entry or exit points.

* * * * *